United States Patent [19]

Stove

[11] Patent Number: 5,453,929
[45] Date of Patent: Sep. 26, 1995

[54] CONTROL SYSTEM WITH DRIVER MONITOR

[75] Inventor: Andrew G. Stove, Reigate, England

[73] Assignee: U.S. Philips Corporation, New York, N.Y.

[21] Appl. No.: 987,895

[22] Filed: Dec. 4, 1992

[30] Foreign Application Priority Data

Dec. 6, 1991 [GB] United Kingdom ............... 9126078

[51] Int. Cl.$^6$ .................... G08B 21/00; A61B 5/04
[52] U.S. Cl. .................. 364/424.01; 364/413.04; 340/571; 340/575; 128/706; 128/744
[58] Field of Search ............ 364/424.01, 424.04, 364/413.02, 413.03, 413.04; 128/687, 689, 703, 706, 734, 744; 340/571, 575, 576

[56] References Cited

U.S. PATENT DOCUMENTS

| | | | |
|---|---|---|---|
| 3,731,672 | 5/1973 | McIntosh | 128/703 |
| 4,004,290 | 1/1977 | Kobayashi et al. | 340/576 |
| 4,088,125 | 5/1978 | Forgione et al. | 128/734 |
| 4,210,905 | 7/1980 | Coons | 340/575 |
| 4,219,800 | 8/1980 | Le Viness | 340/457 |
| 4,232,682 | 11/1980 | Veth | 364/413.03 |
| 4,259,665 | 3/1981 | Manning | 340/575 |
| 4,355,385 | 10/1982 | Hampshire et al. | 370/85.6 |
| 4,485,375 | 11/1984 | Herhberger | 340/576 |
| 4,572,207 | 2/1986 | Yoshimi et al. | 128/706 |
| 4,664,127 | 5/1987 | Ikeyama | 128/689 |
| 4,706,072 | 11/1987 | Ikeyama | 340/576 |
| 4,928,090 | 5/1990 | Yoshimi et al. | 128/734 |

FOREIGN PATENT DOCUMENTS

| | | |
|---|---|---|
| 0014556 | 1/1980 | European Pat. Off. . |
| 2485364 | 6/1980 | France . |
| 2498999 | 8/1982 | France . |
| 2555042 | 6/1977 | Germany . |

OTHER PUBLICATIONS

Practical Wireless, Jun. 1973, p. 134.

Primary Examiner—Kevin J. Teska
Assistant Examiner—Tan Q. Nguyen
Attorney, Agent, or Firm—Robert J. Kraus

[57] ABSTRACT

A vehicle control device such as a steering wheel is equipped with a number of sensors for sensing physiological variations in the human vehicle operator. These sensors are coupled to a master unit (not shown). A rise in the anxiety level of the human operator, which may be due to an impending maneuver, is detected by the master unit via, for example, a rise in skin conductivity, and a signal is provided to other in-vehicle equipment. This signal may be used to delay the provision of non-critical information to the operator, such as navigational data, fuel consumption details or the ringing of a car-telephone.

16 Claims, 4 Drawing Sheets

5,453,929

CONTROL SYSTEM WITH DRIVER MONITOR

BACKGROUND OF THE INVENTION

The present invention relates to a control system for a vehicle having particular, but not exclusive, application to a vehicle information system which varies the kind and quantity of information provided to a driver or other human operator dependent upon that person's other potential actions.

The actions of a car driver or other human vehicle operator can be determined relatively straightforwardly via sensors coupled to the controls of the vehicle, for example, the accelerator pedal, the gearstick etc. However, there is no known simple way of anticipating a driver's reactions or of sensing what may be a crucial moment in mid-journey when he or she least needs other distractions.

Systems for detecting changes in the stress level of a human being are known, for example, lie detectors. Such a device is described in Practical Wireless June, 1973 at page 134. The device comprises a number of electrodes to be held by a person undergoing interrogation and a bridge circuit for measuring the variation in skin conductivity between the electrodes. A substantial change in conductivity is a good indication that the person is lying. However such a technique requires a person participating in the lie detector test to hold separate electrodes which makes such a device unsuitable for anticipating the potential actions of a driver when controlling a vehicle.

SUMMARY OF THE INVENTION

It is an object of the present invention to be able to provide anticipation of a human vehicle operator's actions without any special action being taken by the operator.

According to the present invention there is provided a control system for a vehicle, comprising a master unit and a man-machine interface comprising a device to be held by a human operator during vehicle operation which device comprises at least one transducing means for converting a physiological variation in the human operator to an electrical signal, which means is arranged to supply a signal representative of the physiological variation to the master unit.

By using a physiological variation sensor at a point where a human operator normally holds a device for controlling a vehicle, no special action, such as holding separate electrodes, need be taken by the operator. Various devices for determining physiological variations may be employed as the transducing means. For example strain gauges may be built into one of the vehicle's controls such as a steering wheel or joystick to sense the strength of grip. Skin conductivity sensors may be used as an alternative and sensors made from strips of copper have been found to provide a good electrical contact with human skin. A plurality of sensors may be used to allow for different parts of the vehicle control to be held during normal vehicle operation.

One function of the signal representative of the human operator's physiological variations is to determine the relative priorities of information which must be given to him or her, dependent on what he or she is doing at the time. For example the vehicle information system may inhibit the provision of non-urgent information to the driver, for example, if he or she is suspected to be about to execute a manoeuvre or approach a difficult situation. Both of these instances are believed to cause a rise in the physiological stress level of a human vehicle operator and detection of this rise in stress may be used to delay, for example, the ringing of a cellular telephone or the provision of navigational or fuel consumption information, until the difficult situation has been negotiated.

A plurality of transducing means may be arranged in the vehicle's control so that deliberate variation in contact with the control may be effected on the part of a human operator to control another in-vehicle device. For example, if a number of transducing means were included around the periphery of a car steering wheel the driver could tune the radio without removing his or her hands from the wheel.

Since the vehicle controls will often be quite free to move in use, making an electrical connection between the transducing means and the master unit may sometimes cause difficulty. If other control devices, for example a horn button in a car steering wheel, are already mounted in the vehicle control, the wiring of the transducing means may be shared with that for the other control device.

BRIEF DESCRIPTION OF THE DRAWING

Embodiments of the invention will now be described, by way of example, with reference to the accompanying drawing figures, in which.

DESCRIPTION OF THE PREFERRED EMBODIMENTS

Figure 1:
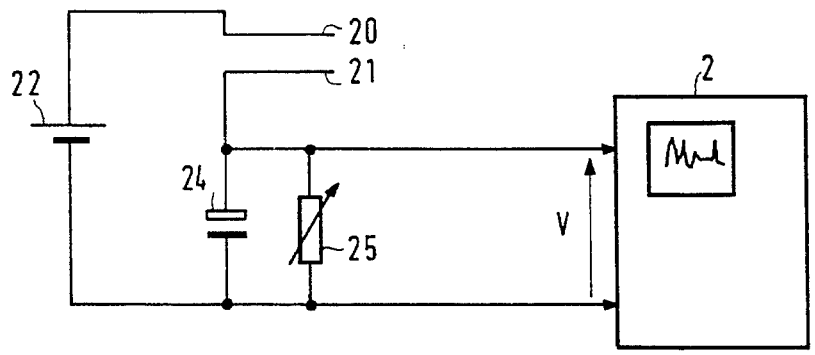
FIG. 1 shows a test circuit for measuring a driver's skin conductivity.
Figure 3:
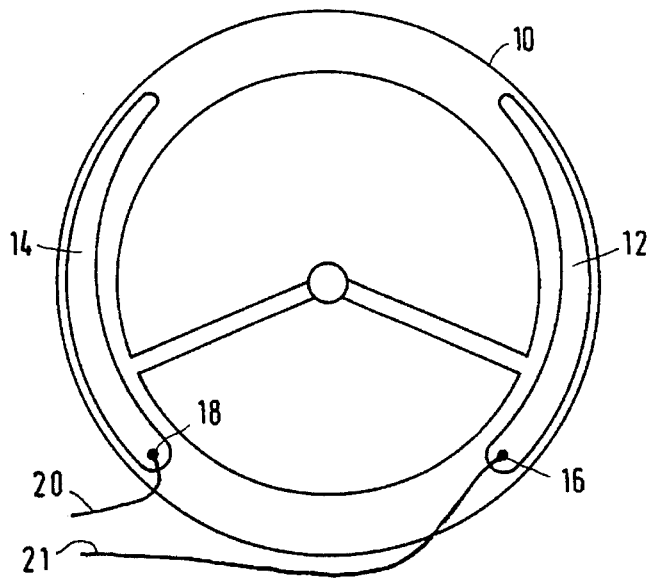
FIG. 3 shows a steering wheel with a pair of contacts for use in a system in accordance with the present invention.

FIG. 1 shows a test circuit for measuring the conductivity of a driver's skin which is to be used in conjunction with a steering wheel 10 as shown in FIG. 3, for a car or boat. The wheel has a pair of arcuate electrodes 12,14 diametrically mounted in or on the rim of the wheel. The electrodes conveniently comprise copper strips nominally 10 mm. wide and each of a length corresponding to approximately a quarter to a third of the circumference of the steering wheel. These electrodes are mounted so as to make good physical and electrical contact with a driver's hands as he or she holds the wheel. Connections are made between the electrodes 12,14 and two wires 21, 20 at points 16,18 respectively and these wires are coupled to the test circuit of FIG. 1.

In FIG. 1 the first of the two wires go is connected to the positive terminal of a battery 22 whose negative terminal is connected to the negative plate of a 1.5 µF electrolytic capacitor 24, to one terminal of a 100 kOhm variable resistor 25 and to one of the Y inputs of an oscilloscope 2. The second of the two wires 21 is connected to the positive plate of the capacitor 24, the remaining terminal of the resistor 25 and to the other Y input of the oscilloscope 2. The voltage applied to the oscilloscope is denoted by the letter V.

By virtue of holding both electrodes 12,14 (FIG. 3) the skin conductivity of the driver appears between the wires 20,21 and this conductivity forms a potential divider across the battery 22 with the resistor 25. The voltage at the centre point of the divider is measured by the oscilloscope 2 which may be a digital storage device. The sensitivity of the test circuit may be adjusted by varying the resistance of the resistor 25. The capacitor 24 is intended to smooth out noise and hum which may be picked up by the electrodes from within the vehicle.

Figure 2:
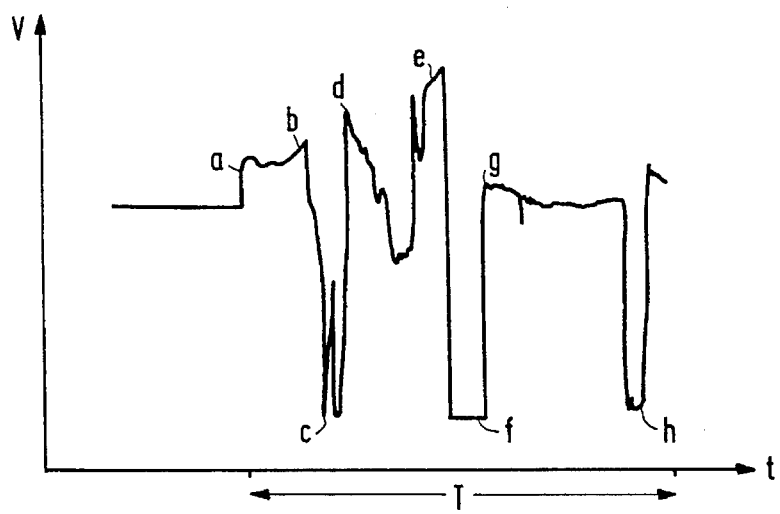
FIG. 2 shows an oscilloscope trace of a driver's skin conductivity over a period of time.

FIG. 2 shows an output trace of the oscilloscope 2 shown in FIG. 1 while the test arrangement was installed in a car. The X-axis of the trace represents time t and the Y-axis represents the voltage V at the input to the oscilloscope. The voltage V is dependent upon the skin conductivity applied between the electrodes 12,14 (FIG. 3). The portion of the trace labelled T corresponds to about 70 seconds of driving and has the following features. The start of the trace is labelled a and there then follows a few seconds of uneventful conductivity measuring until the occurrence of a discernable ramp up lasting about one second at b. The trace then flickers briefly down to its lowest point at c as the driver loosens his grip on the wheel to operate the indicator stalk. The trace returns to uneventful conductivity measurement at d until another discernable rise in conductivity over about one second at e. At f the trace exhibits its lowest value for several seconds as the driver changes gear causing him to remove his hand from the steering wheel and the trace resumes normal measuring at g. There then follow several seconds of normal measuring until another flicker at h as the driver momentarily removes one hand from the wheel.

As can be observed there is a slight but noticeable rise in skin conductivity over approximately one second immediately before the driver executes a manoeuvre. This is thought to be due to two factors:

i) the steering wheel is gripped more tightly, improving the electrical connection, and ii) as anxiety level increases the palms of the driver's hands produce more perspiration, increasing the skin conductivity between the hands and the electrodes.

Figure 4:
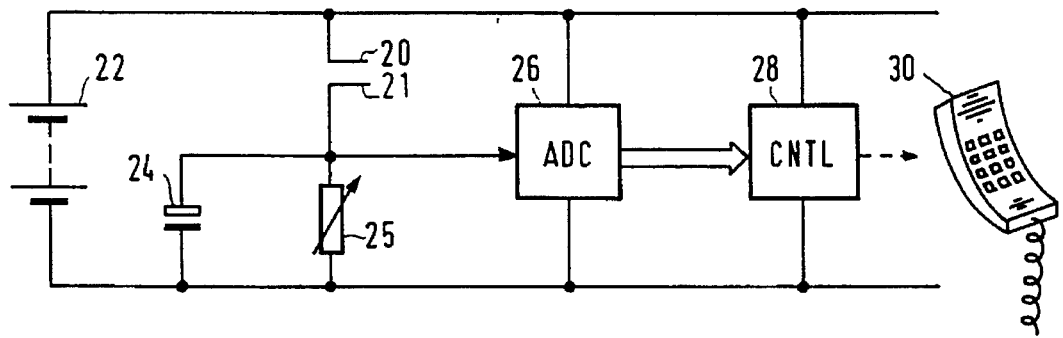
FIG. 4 shows a master unit for use with the steering wheel shown in FIG. 3.

FIG. 4 shows a master unit for use with the steering wheel shown in FIG. 3. A battery 22 provides power for the master unit and has a positive terminal which is connected to one of the wires 20, to the positive supply terminal of a slow speed analogue to digital converter (ADC) 26 and a control unit (CNTL) 28 including a computer for determining what information to give to the driver. The other wire 21 is connected to the positive plate of a 1.5 µF electrolytic capacitor 24, to a first terminal of a 100K variable resistor 25 and to an input terminal to the ADC 26. A negative terminal of the battery 22 is connected to the negative plate of the capacitor 24, to the remaining terminal of the resistor 25 and to the negative supply terminals of the ADC 26 and CNTL 28. A digital output of the ADC 26 is fed to the CNTL 28 which has a control output shown in broken lines for inhibiting the ringer of a cellular telephone 30.

Additionally or alternatively, navigational information and fuel consumption information, for example, may be prevented from being displayed.

In operation, the master unit senses a variation in the skin conductivity between the hands of a driver due to physiological stress which may give rise to firmer gripping of the wheel and increased perspiration. The CNTL 28 then determines whether a significant variation in driver skin-conductivity has occurred. The driver's skin conductivity forms a potential divider with the variable resistance 25 to vary the voltage at the input of the ADC 26. The resistor 25 may be adjusted to alter the sensitivity of the master unit. The capacitor 24 provides a damping action to remove noise and hum as before. A short, reasonably fast rise in skin conductivity, as shown at b and e in FIG. 2, is an indication of increased likelihood of an impending manoeuvre. A relatively simple sensing routine within the CNTL 28 detects such a rise and provides an inhibit signal to prevent the display of non-urgent information until the skin-conductivity of the driver returns to normal or near normal.

Figure 5:
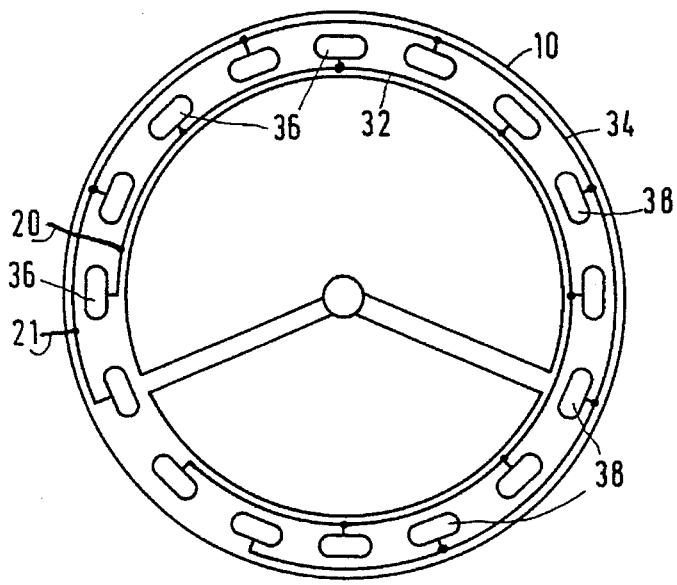
FIG. 5 shows a steering wheel with a large number of transducing means.

The layout of the electrodes on the steering wheel shown in FIG. 3 has the disadvantage that if the driver removes one hand from the wheel, all monitoring of his or her physiological variations is lost. FIG. 5 shows an alternative electrode layout on a steering wheel 10. An even plurality, for example 16, of electrodes 36,38 are disposed equally spaced around the periphery of the wheel 10. A first set of alternately positioned electrodes 36 are connected together by a common connector 32 and a second set of alternately positioned electrodes 38 are connected together by a common connector 34. The connectors 32 and 34 are coupled electrically to a pair of wires 20,21 for connection to the master unit (FIG. 4). With this arrangement at least one electrode of each set will be bridged even if the driver has only one hand on the steering wheel. In addition the master unit may be arranged to sense an approximate halving of the conductivity of the driver's skin which is due to a removal of one hand from the wheel. If such a reduction in conductivity occurs, the master unit may reasonably conclude the driver is actually executing a manoeuvre, for example a gear change, and the master unit may provide an inhibit signal accordingly. As will be appreciated an odd plurality of electrodes could also be used. Having two electrodes connected together which are adjacent will not usually be critical, particularly if they are placed at the bottom of the steering wheel, for example.

Figure 6:
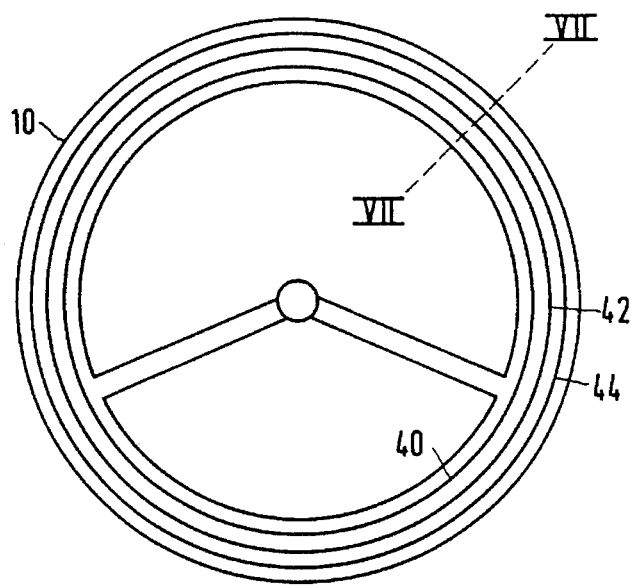
FIG. 6 shows a steering wheel including an alternative arrangement of transducing means.
Figure 7:
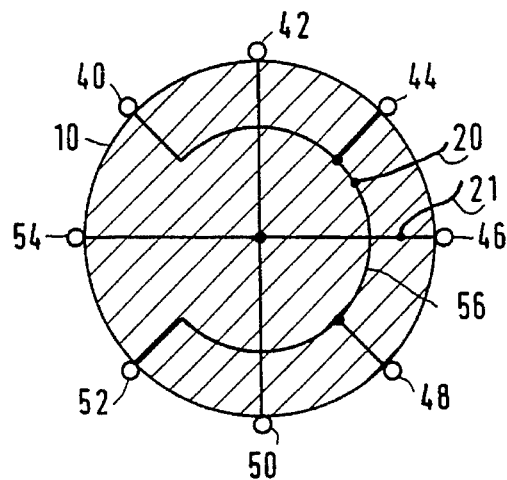
FIG. 7 is a section through the steering wheel of FIG. 6 taken on the line VII—VII, which shows the interconnection of the transducing means.

FIGS. 6 and 7 show a further variation in the layout of electrodes on a steering wheel 10. The electrodes 40–54 are in the form of thin continuous wires extending circumferentially around the periphery of the wheel so as not to come into contact with each other at any point. As shown in FIG. 7 the wires are joined together in two alternating sets which are coupled to a master unit via a pair of wires 20,21. Again, a single hand on the wheel will continue to provide physiological variation information and halving of the overall conductivity will indicate the removal of one of the driver's hands from the wheel.

The electrodes illustrated in the FIGS. 3 and 5 to 7 may be realised using metallic contacts or a conductive rubber which have been found to make good electrical contact with human skin.

When making a skin conductivity measurement, it may be desirable to power the sensing arrangement via a stabilised voltage supply so that voltage variations in the vehicle supply do not cause the human operator any unpleasant sensations.

All of the embodiments of the present invention thus far described rely upon making an electrical connection between the driver's hand and a vehicle control, for example a steering wheel. If a driver is wearing gloves these embodiments will not function correctly.

Figure 8:
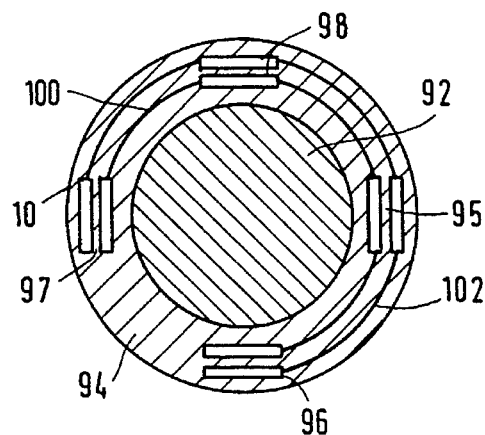
FIG. 8 shows a sectional view of a steering wheel having an alternative type of transducing means.

FIG. 8 shows a section through a steering wheel 10 which comprises a solid core 92 and a softer, slightly compressible outer section 94. Within the outer section there are disposed capacitors 95,96,97,98 which each comprise two plates substantially parallel to the surface of the wheel. The inner plates of the capacitors are connected together by a common connector 100 and the outer plates are connected together by a common connector 102. These two connectors are coupled electrically to a master unit (not shown). The capacitors 95–98 act as strain gauges since the separation of their plates may be reduced from a quiescent position by applying a squeezing force to the outside surface of the steering wheel 10. Variations in the capacitances of the capacitors may be monitored in various ways, for example, by including them in an oscillator circuit and monitoring its output frequency or by a capacitance bridge circuit. Increases in the strength of the grip applied to the wheel are detected from the output of strain gauges and action is taken by a control unit as desired. By basing the physiological measurement on grip, the system still operates even if a vehicle operator is wearing gloves. Other types of strain gauges may be used in an equivalent manner to those described, for example, resistive, piezoelectric (or magnetostrictive) and electromagnetic types.

Figure 9:
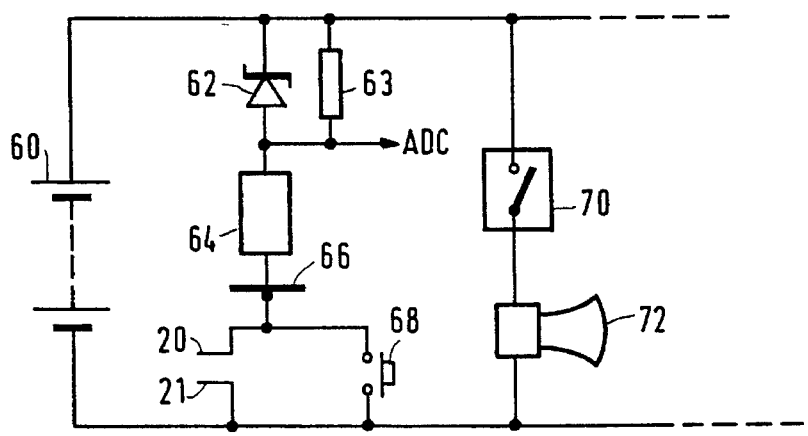
FIG. 9 shows a circuit arrangement which permits the wiring from a transducer to be shared with an in-vehicle control.

FIG. 9 shows a circuit arrangement which permits a connection between electrodes in a steering wheel and a master unit (not shown) using existing vehicle wiring, for example that for the horn push button. A car battery 60 has a positive terminal connected to the cathode of a 2.3 v zener diode 62, to a first terminal of a 5 kOhm resistor 63 and to one terminal of a set of relay contacts 70. A negative terminal of the battery 60 is connected to a first wire 21, to a first terminal of a horn push button 68 and to a first terminal of a horn 72. The anode of the diode 62 is connected to the remaining terminal of the resistor 63, to an input to an ADC (not shown) and to a first terminal of a relay coil 64 of the relay contacts 70. The electrical resistance of the relay coil 64 is much less than that of the resistor 63. The remaining terminal of the relay coil 64 is connected to one of a pair of sliding contacts 66. The other of the pair of contacts is connected to a second wire 20 and the second terminal of the push button 68. Another terminal of the relay contacts 70 is connected to a second terminal of the horn 72.

In normal operation the horn button 68 is open circuit and a driver's skin conductivity is applied between the wires 20,21. Since the resistance of the relay coil 64 is much lower than that of the resistor 63 little voltage will be dropped across it and a potential divider is effectively formed between the resistor 63 and the skin conductivity of the driver. The comparatively small voltage dropped across the resistor 63 will be insufficient to cause the zener diode 62 to break down. The conductivity measurement is carried out, as previously, by an ADC connected to measure the voltage at the centre of the potential divider.

To operate the horn of the vehicle the push button 68 is pressed and this applies the full battery voltage across the relay coil 64 and the zener diode 62. The zener diode 62 breaks down, short circuiting the resistor 63 and a relatively large current flows through the relay coil closing the contacts 70 and sounding the horn 72.

Capacitance measurements, for example if the sensor in the steering wheel comprises a strain gauge, may be made between the negative terminal of the battery 60 and the second terminal of the relay coil 64. In this case the zener diode 62 and the resistor 63 may be eliminated and the first terminal of the relay coil 64 connected directly to the positive battery terminal.

Figure 10:
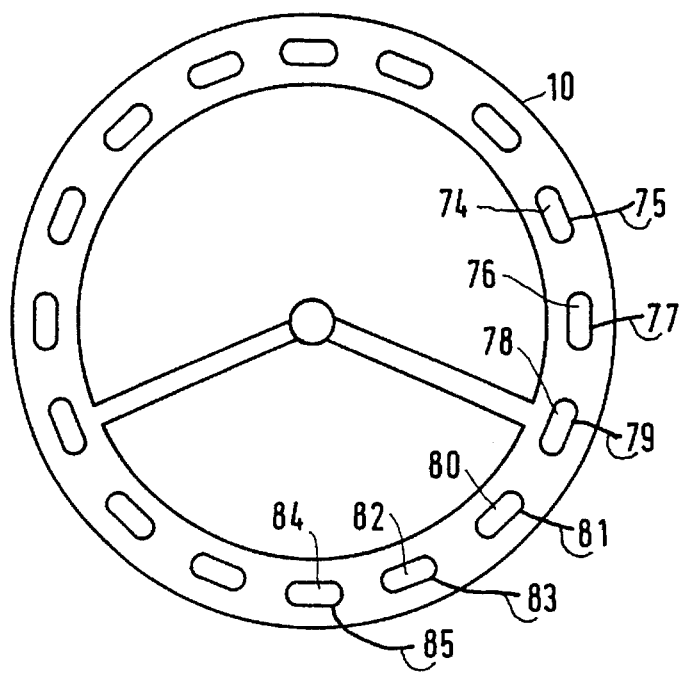
FIG. 10 shows a steering wheel similar to that shown in FIG. 3 but which has a different connection arrangement.

In addition to sensing physiological variations in the driver, the present invention may additionally provide for him or her to control other vehicle functions without removing either hand from the steering wheel. FIG. 10 shows a steering wheel 10 having a plurality of electrodes 74,76,78, 80,82,84 mounted around its periphery, which electrodes are connected to wires 75,77,79,81,83,85 respectively. The conductivity between adjacent pairs of the electrodes will vary depending on the position of the driver's hands on the wheel and this may be sensed and converted to a signal for controlling other vehicle functions, for example tuning the radio. In addition the conductivity between the electrodes as a whole is measured to predict likely vehicle manoeuvres and difficult situations as before.

To use such an arrangement means must be provided to prevent normal manoeuvring of the vehicle from disturbing the settings of the vehicle functions controlled by it. One solution is to display impending changes to those vehicle function settings on the dashboard of the vehicle and giving the driver the option to implement or discard the changes, for example by quickly touching a stalk switch mounted close to the steering wheel. Such a stalk switch could also be arranged so that it must be operated briefly before the driver wishes to make changes in vehicle function settings. Alternatively, the control electrodes for vehicle functions could be located on the spokes of the wheel or even in the centre. As another alternative the sensing of changes in vehicle function settings could be responsive only to a certain pattern of taps or squeezes applied to the wheel by the driver which pattern is unlikely to occur during normal driving. A further solution could be based upon the overall physiological measurement derived from the driver so that changes in the pattern of grip applied to the wheel while the driver's physiological measurement is stable are used to alter vehicle function settings and changes applied just after or during significant variations in the physiological measurement are assumed to be due to vehicle manoeuvring and are ignored.

Figure 11:
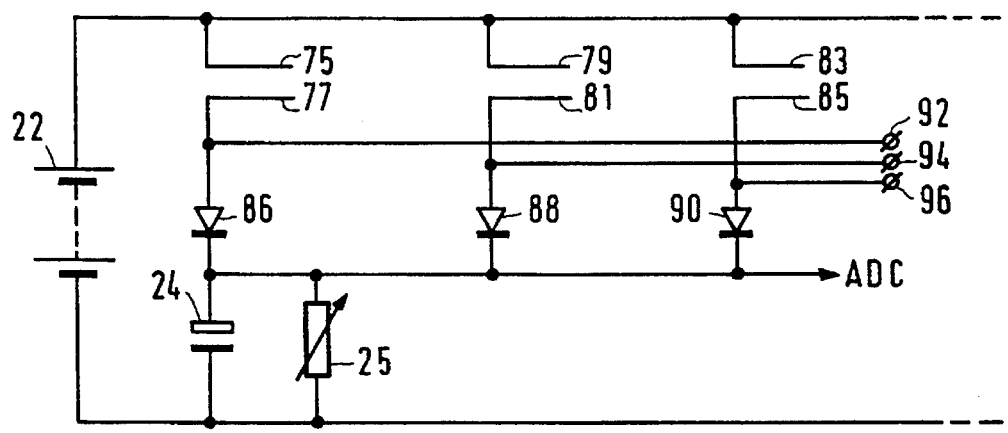
FIG. 11 shows a circuit arrangement for use with the steering wheel shown in FIG. 10.

FIG. 11 shows a circuit arrangement suitable for providing a control signal for vehicle functions and also an overall conductivity measurement. A battery 22 has a positive terminal which is connected to the first wire 75;79,83 of each of three pairs of wires. The second wire 77,81,85 of each of the pairs of wires are connected to the anodes of three diodes 86,88,90. The cathodes of the diodes 86,88,90 are connected together to the positive plate of a 1.5 μF electrolytic capacitor 24 and to a first terminal of a 100 kOhm variable resistor 25. The negative plate of the capacitor 24 and the second terminal of the resistor 25 are connected to the negative terminal of the battery 22.

In operation a signal from the positive plate of the capacitor 24 is fed to an ADC as in FIG. 4 for the driver physiological variation sensing. Further, independent sensing of the same type is applied to the terminals 92,94,96 connected to the anodes of the diodes. Variations in the voltages at these terminals may be sensed to determine whereabouts the driver is holding the wheel and a control unit (not shown) may be used to convert these measurements into a combined control signal. The sensing applied to the terminals 92,94,96 must be of the same type as that applied overall, in other words via a finite resistance to ground. Even a high resistance path between the terminals and the positive supply rail will bias the diodes into conduction and upset circuit operation.

A much larger number of contacts around the wheel than shown in the FIGS. 5 and 10 may each be connected with a diode and an additional terminal in this way to provide a more selective control.

Other types of sensor may be used as an alternative to conductivity sensors in this control arrangement, for example strain gauges described previously.

From reading the present disclosure, other modifications will be apparent to persons skilled in the art. Such modifications may involve other features which are already known in the design, manufacture and use of control systems for vehicles and component parts thereof and which may be used instead of or in addition to features already described herein. Although claims have been formulated in this application to particular combinations of features, it should be understood that the scope of the disclosure of the present application also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

I claim:

1. A control system for a vehicle, comprising: a master unit for supplying information to a human operator of the vehicle and a man-machine interface comprising a device to be held by the human operator during vehicle operation, which device comprises at least one transducing means for converting a physiological variation in the human operator to an electrical signal, and means for inhibiting the supply of an information signal to the vehicle operator in response to the electrical signal representative of the physiological variation.

2. A control system as claimed in claim 1, wherein the transducing means comprises at least one strain gauge.

3. A control system as claimed in claim 1, wherein the transducing means comprises a means for measuring skin conductivity.

4. A control system as claimed in claim 3, wherein the means for measuring conductivity include at least an electrode comprising conductive rubber.

5. A control system as claimed in claim 3, wherein the means for measuring conductivity includes at least an electrode comprising a metallic contact.

6. A control system as claimed in claim 1 wherein said inhibiting means is operable to determine relative priorities of information and is responsive to the electric signal representative of the physiological variation so as to provide information having a low priority to the human operator at times of low physiological variation.

7. A control system as claimed in claim 6, comprising a plurality of transducing means for determining where the device is held by the human operator, and means coupled to the plurality of transducing means for deriving a signal representative of that location.

8. A control system as claimed in claim 7, wherein the vehicle has wiring and the master unit comprises means for obtaining a signal from the transducing means via a part of said vehicle wiring.

9. A control system as claimed in claim 8, wherein the part of said vehicle wiring comprises the horn wiring.

10. A control system as claimed in claim 1, comprising a plurality of transducing means for determining where the device is held by the human operator, and means coupled to the plurality of transducing means for deriving a signal representative of that location.

11. A control system as claimed in claim 1, wherein the vehicle has wiring and the master unit comprises means for obtaining a signal from the transducing means via a part of said vehicle wiring.

12. A control system as claimed in claim 11, wherein the part of said vehicle wiring comprises the horn wiring.

13. The control system as claimed in claim 1 wherein said device comprises the vehicle steering wheel and the transducing means comprises; a slightly compressible annular member on said steering wheel, a plurality of pairs of electrodes located within said annular member at circumferentially spaced points and spaced apart to form a plurality of variable capacitors whose capacitance is varied as a function of the gripping force applied to the steering wheel by the vehicle operator, one set of capacitor electrodes being connected together to the master unit and the other set of capacitor electrodes being connected together and to the master unit.

14. A control system for a vehicle comprising:

a master unit for supplying information to a human operator of the vehicle, a device to be held by the vehicle operator to provide manual control of the vehicle during operation thereof, transducing means coupled to said master unit and associated with said manual control device and arranged to convert a variation in a physiological characteristic of the human operator into a corresponding electric signal, and means for inhibiting the supply of an information signal to the vehicle operator in response to the electric signal.

15. The control system as claimed in claim 14 wherein said transducing means comprises at least two electrode elements arranged for contact by the vehicle operator so as to provide an indication of the skin conductivity of the operator, said electrode elements being part of a resistive voltage divider coupled to a source of operating voltage for the vehicle.

16. The control system as claimed in claim 14 wherein said inhibiting means determines relative priorities of information and is responsive to the electric signal so as to provide information having a low priority to the human operator only at times of low physiological variation.

* * * * *